US009611177B2

(12) United States Patent
Soens et al.

(10) Patent No.: US 9,611,177 B2
(45) Date of Patent: *Apr. 4, 2017

(54) MICROCAPSULES AND CONCRETE CONTAINING THE SAME

(71) Applicants: Devan Chemicals NV, Ronse-Renaix (BE); Universiteit Gent, Ghent (BE)

(72) Inventors: Hugo Soens, Kaster (BE); Nele De Belie, Brakel (BE); Jianyun Wang, Ghent (BE); Maxime Durka, Ronse (BE)

(73) Assignees: UNIVERSITEIT GENT, Ghent (BE); DEVAN CHEMICALS NV, Ronse-Renaix (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/962,638

(22) Filed: Aug. 8, 2013

(65) Prior Publication Data
US 2014/0248681 A1  Sep. 4, 2014

(30) Foreign Application Priority Data

Mar. 1, 2013  (GB) .................................. 1303690.0

(51) Int. Cl.
| C04B 24/00 | (2006.01) |
| C04B 20/10 | (2006.01) |
| C04B 40/06 | (2006.01) |
| C12N 11/04 | (2006.01) |
| C12N 1/20 | (2006.01) |
| C04B 103/00 | (2006.01) |

(52) U.S. Cl.
CPC .......... *C04B 24/00* (2013.01); *C04B 20/1029* (2013.01); *C04B 20/1033* (2013.01); *C04B 40/0675* (2013.01); *C12N 1/20* (2013.01); *C12N 11/04* (2013.01); *C04B 2103/0001* (2013.01)

(58) Field of Classification Search
None
See application file for complete search history.

(56) References Cited

FOREIGN PATENT DOCUMENTS

| CN | 102584073 | 7/2012 |
| CN | 103043937 | 4/2013 |
| EP | 2082999 | 7/2009 |
| EP | 2239242 | 10/2010 |
| WO | WO 2009/098091 | 8/2009 |
| WO | WO 2010/142401 | 12/2010 |
| WO | WO 2011/126361 | 10/2011 |

OTHER PUBLICATIONS

Hu et al., Materials Chemsitry and Physics, vol. 118 (2009) 63-70.*
Sarda et al., J. Ind. Microbiol. Biotechnol. (2009) vol. 36: 1111-1115.*
Shelvay et al., Thesis, Massachusetts Institute of Technology, Jun. 2012, pp. 1-46.*
Yang et al., Proc. of SPIE vol. 7493 (2009) pp. 74934L-1 to 74934L-12.*
"Derivative." Merriam-Webster.com. Merriam-Webster, n.d. Web. Oct. 10, 2014. <http://www.merriam-webster.com/dictionary/derivative>.*
Van Tittelboom et al., Use of bacteria to repair cracks in concrete, Cement and Concrete Research, vol. 40, 2010, pp. 157-166.*
Yang et al., A self-healing cementitious composite using oil core/silica gel shell microcapsules, Cement & Concrete Composites, vol. 33, 2011, pp. 506-512.*
Bang et al., "Calcite precipitation induced by polyurethane-immobilized Bacillus pasteurii", Enzyme and Microbial Technology, vol. 28, Jan. 1, 2001, p. 404.
International Search Report and Written Opinion dated Jun. 12, 2014 issued for International PCT Application No. PCT/EP2014/054100.
UK Intellectual Property Office Search Report dated Aug. 30, 2013 issued for UK Patent Application No. GB 13036900.
Zemskov et al, "Two analytical models for the probability characteristics of a crack hitting . . . " pp. 3323-3333, Computational materials science vol. 50, No. 12, Jun. 2011.
Jianyun Wang et al, "Use of silica gel or polyurethane immobilized bacteria for self-healing concrete", pp. 532-540, Construction and Building Materials, vol. 26, Dec. 2012.

* cited by examiner

*Primary Examiner* — Yvonne Pyla
(74) *Attorney, Agent, or Firm* — K&L Gates LLP

(57) ABSTRACT

Microcapsules for inclusion in concrete are disclosed. The microcapsules are adapted to reduce the area of defects in the concrete. The microcapsules may include carbonatogenic bacteria spores in a liquid core, contained in a polymer layer. Also disclosed are concrete compositions including the microcapsules.

36 Claims, 7 Drawing Sheets

MICROCAPSULES AND CONCRETE CONTAINING THE SAME

CROSS-REFERENCE TO A RELATED APPLICATION AND PRIORITY CLAIM

This application claims the priority under at least 35 U.S.C. 119 to United Kingdom Patent Application No. 1303690.0 filed on 1 Mar. 2013.

The present invention relates to microparticles, especially microcapsules, for inclusion in concrete or like materials, containing microorganisms in the form of bacterial spores and/or bacterial nutrients, which microparticles are adapted to reduce, or to assist in the reduction of, the area of a defect in said concrete (or like material) once a quantity of said microparticles has fractured/ruptured. The invention also relates to a concrete or like material composition containing a quantity of such microparticles, especially microcapsules, which is "self-healing" in respect of any defects therein.

Concrete, concrete-based and concrete-like materials are often used in civil engineering projects as the building material of choice because of their high compressive strength, high durability and low cost. Projects in which such materials are used include constructions such as bridges, road projects, underground projects, water conservancy and hydropower projects, nuclear power plants, ports and marine engineering, etc, as well as smaller scale projects such as ramps, paving slabs, etc. Constructions which include concrete or like materials typically have long lifetimes (of at least 50 years), however, in this time frame usage and the influence of external environmental factors can lead to defects forming therein. Defects include visible cracks (of millimeters in width), micro-cracks (of micrometers in width), indentations and crevices. If left untreated, one or more of such defects could reduce the lifetime of a construction and/or may pose an immediate threat to the safety of said construction and its users.

Although a concrete composition per se may be optimized to improve its inherent defect resistance, for example by appropriate selection of the raw materials used, their mixing ratio, inclusion or omission of particular additives, the manufacturing process, casting processes and methods, defects are known to still occur with varying degrees of severity and over the course of varying numbers of years since setting of the concrete. Therefore, the timely and effective repair of defects in concrete and like material is of continued concern to those in the field, including scientists and engineers.

It is known that under certain circumstances, some concrete compositions may exhibit a degree of autogenous healing, i.e. autogenous repair, of defects therein. Typically, with relatively freshly laid concrete and high strength concrete, un-hydrated cement particles are present in the concrete matrix; when water becomes available in defects that may have formed in such concrete, any un-hydrated cement particles present in/on the defect begin to hydrate, leading to a certain degree of healing or repair of the defect in question. In general, it is thought that there are two mechanisms by which autogenous repair may occur based around secondary hydration of un-hydrated cement particles present in the concrete composition: (1) the consequential precipitation of calcium carbonate, and (2) swelling of the hydration products to decrease the area of the defect. With mechanism (1), carbon dioxide ($CO_2$) from the surrounding atmosphere may dissolve in water to generate carbonate anions ($CO_3^{2-}$) in the alkaline environment of the concrete (the pH of concrete is around 12.5~13). Free dissolved calcium cations ($Ca^{2+}$) arising from the defect may then react with the carbonate anions to form calcium carbonate. However, any such autogenous healing is greatly dependent on the age of the concrete, the water to cement ratio and the available water in the vicinity of the defect.

It is also known, for example from EP2239242A1, to provide a self-repairing or "self-healing" concrete which has distributed throughout a number of urea-formaldehyde, melamine-formaldehyde and/or urea-melamine-formaldehyde resin polymer microcapsules containing adhesive. The disclosed adhesives include mono-component adhesives, such as polyurethanes, organo-silico anaerobes, acrylic resins, and chloroprene rubbers, and multi-component adhesives, such as epoxy resins. Once a crack occurs in the concrete, microcapsules in the vicinity of the crack rupture due to induced stress caused by the crack, releasing the encapsulated adhesive to repair the crack.

However, a number of technical problems may be encountered and require a solution to be provided with such teaching, including interface compatibility between the walls of the crack in the concrete and the adhesive materials used for repair, the extent to which the adhesive will flow to repair the crack prior to it setting, the durability of the adhesive, and the consequential effects (such as localized weakening) on the concrete immediately surrounding the repaired crack.

Accordingly, there is still a need to address the repair of defects in concrete and like materials, preferably by means of auto-reparation so as to avoid the need for human or mechanical intervention in the identification and actioning of a repair, in as timely a manner as possible to provide a compatible and durable solution.

First Aspect

In a first aspect, the present invention thus provides microparticles, for inclusion in concrete, concrete-based material and concrete-like material, adapted to reduce, or to assist in the reduction of, the area of a defect in said material once a quantity of said microparticles has fractured or is exposed at an interface of the defect, said microparticles each comprising:

a core, in the form of a porous solid and/or a liquid, having carbonatogenic bacterial spores and/or bacterial nutrients dissolved and/or dispersed therein.

Thus the core may be a porous solid, in which case it may or may not be provided with a surrounding shell, i.e. there may be a shell which surrounds the porous solid core, or the core may be a liquid, it which case it may be provided with a surrounding shell, i.e. the shell may encapsulate the liquid core therein. Alternatively, the core may be a porous solid having liquid present in substantially all of its pores, surrounding which there may be provided a surrounding shell.

For the avoidance of any doubt, said core may have carbonatogenic bacterial spores dispersed therein in the absence of any bacterial nutrients (which may be provided in the concrete or like material from another source), or said core may have bacterial nutrients dispersed and/or dissolved therein in the absence of any bacterial spores (which may be provided in the concrete or like material from another source), or said core may have both bacterial spores and bacterial nutrients dissolved and/or dispersed therein. Once released, the bacterial nutrients are readily available to act with atmospheric oxygen and ambient water to enable germination of the bacterial spores to form vegetative bacteria, thus facilitating calcium carbonate production, as will be described in more detail later in the specification The "other source" of bacterial nutrients includes other microparticles containing said nutrients and naturally occurring, environmental nutrients found in situ. The "other source" of carbonatogenic bacterial spores includes other microparticles containing said spores and naturally occurring, environmental spores found in situ.

A "microparticle" as described herein is a particle with dimensions from $1 \times 10^{-7}$ m to less than $1 \times 10^{-3}$ m, i.e. from 0.1 to less than 1000 μm, which may be spherical or non-spherical.

Such microparticles have the ability, once included in a concrete or like material composition, to reduce, or assist in the reduction of, the area of a defect, such as a crack or an indentation therein, once a quantity of said microparticles has fractured. Fracture of the microparticles is achieved by locally induced internal stress in the concrete around the area of the defect, however, an external influence such as force or increased/decreased temperature, may be applied in addition to the internal stress to act on the inherent friability of the microparticles to achieve fracture. Once fractured, the relevant microparticles will release their dissolved and/or dispersed contents, thus facilitating repair of the defect in as timely a manner as possible to provide a compatible and durable solution.

Second Aspect

In a second aspect of the invention, there are provided microparticles, in the form of microcapsules, for inclusion in concrete, concrete-based material and concrete-like material, adapted to reduce the area of a defect in said material once a quantity of said microcapsules has fractured by rupture or is exposed at an interface of the defect, said microcapsules each comprising:

a polymeric shell encapsulating a liquid core,
wherein the polymeric shell comprises a substantially impermeable polymer layer and the liquid core comprises carbonatogenic bacterial spores dispersed in a liquid, and
wherein at least one of the following criteria (i)-(iii) is fulfilled:
(i) said polymer layer comprises a polymer selected from the group consisting of: gelatines, polyurethanes, polyolefins, polyamides, polysaccharides, silicone resins, epoxy resins, chitosan, aminoplast resins and derivatives and mixtures thereof, and/or
(ii) said bacterial spores are in the form of a microorganism that is capable of reducing the area of the defect by means of mineral or extracellular polymeric substance ("EPS") production, and are preferably selected from the group of bacteria consisting of: *Bacillus cereus, Bacillus subtilis, Bacillus sphaericus, Bacillus lentus, Bacillus pasteurii, Bacillus megaterium, Bacillus cohnii, Bacillus halodurans, Bacillus pseudofirmas, Myxococcus Xanthus* and mixtures thereof, and/or
(iii) said liquid is a non-aqueous, water-immiscible liquid selected from the group consisting of: organic oils, mineral oils, silicone oils, fluorocarbons, fatty acids, plasticizers, esters and mixtures thereof, such that, when a quantity of said microcapsules is present in the material, the area of the defect therein is reducible by at least 45% as compared to an initial area of the defect once at least some of said quantity of microcapsules have been ruptured.

Such microcapsules have the ability, once included in a concrete or like material composition, to reduce the area of a defect, such as a crack or an indentation therein, once a quantity of said microcapsules has ruptured. Rupture of the microcapsules is achieved by locally induced internal stress in the concrete around the area of the defect, however, an external influence such as force or increased/decreased temperature, may be applied in addition to the internal stress to act on the inherent friability of the microcapsules to achieve rupture. Once ruptured, the relevant microcapsules will release their encapsulated contents, thus facilitating repair of the defect in as timely a manner as possible to provide a compatible and durable solution.

Microcapsules according to the invention may be made by any suitable microencapsulation technique known in the art, including, but not limited to, coacervation, interfacial polycondensation polymerization, addition or in-situ emulsion polymerization, addition or in-situ suspension polymerization, spray-drying and fluidized bed-drying to produce microcapsules of a desired size, friability and water-insolubility. Generally, methods such as coacervation and interfacial polymerization can be employed in known manner to produce microcapsules of the desired characteristics. Such methods are described in U.S. Pat. No. 3,870,542, U.S. Pat. No. 3,415,758 and U.S. Pat. No. 3,041,288.

For the avoidance of doubt, the rupture of as few as a single microcapsule would facilitate some degree of defect area reduction, however for the results to be non-negligible and for a discernible reparation to be observed, a quantity of microcapsules (being greater in number than a single microcapsule, preferably at least $10^4$ microcapsules per cm² of defect area, and generally of the order of $10^6$ microcapsules per cm² of defect area) are required to rupture.

Preferably, in microcapsules according to the second aspect of the invention, any two of the three criteria (i)-(iii) may be fulfilled, with criteria (i) and (ii) being preferred. Further preferably however, in such microcapsules all three of criteria (i)-(iii) may be fulfilled.

To achieve the percentage reduction in defect area discussed, in each microcapsule, the concentration of the bacterial spores may preferably be at least $10^9$ spores per gram (dry weight) of microcapsule.

Third Aspect

In a third aspect, the invention provides microcapsules, for inclusion in concrete, concrete-based material and concrete-like material, adapted to reduce the area of a defect in said material once a quantity of said microcapsules has ruptured or is exposed at an interface of the defect, said microcapsules each comprising:

a polymeric shell encapsulating a liquid core,
wherein the polymeric shell comprises a substantially impermeable polymer layer and the liquid core comprises carbonatogenic bacterial spores dispersed in a liquid, and
wherein, in each microcapsule, the concentration of the bacterial spores is at least $10^9$ spores per gram (dry weight) of microcapsule, such that, when a quantity of said microcapsules is present in the material, the area of the defect therein is reducible by at least 45% as compared to an initial area of the defect once at least some of said quantity of microcapsules have been ruptured.

The liquid in which the bacterial spores are dispersed may preferably be a non-aqueous, water-immiscible liquid.

As with the second aspect of the invention, such microcapsules have the ability, once included in a concrete or like material composition, to reduce the area of a defect, such as a crack or an indentation therein, once a quantity of said microcapsules has ruptured, with all the attendant benefits described earlier. Again, such microcapsules may be made by any suitable microencapsulation process, such as those described earlier.

Advantageously, in either of the second or third aspects of the invention, the liquid core of some or all of the microcapsules may further comprise bacterial nutrients, i.e. the nutrients may be co-encapsulated with the carbonatogenic bacterial spores in some or all of the microcapsules. With such co-encapsulation, on rupture of a relevant microcapsule and dispersal of its contents, the bacterial nutrients are readily available to act with atmospheric oxygen and ambient water to enable germination of the bacterial spores to form vegetative bacteria, thus facilitating calcium carbonate production, as will described in more detail later in the specification. Furthermore, encapsulated nutrients may have a less detrimental effect on the surrounding concrete matrix than if the nutrients were freely distributed throughout.

Fourth Aspect

In a fourth aspect, the invention provides microcapsules, for inclusion in concrete, concrete-based material and concrete-like material, adapted to reduce the area of a defect in said material once a quantity of said microcapsules has ruptured or is exposed at an interface of the defect, said microcapsules each comprising:
  a polymeric shell encapsulating a liquid core,
    wherein the polymeric shell comprises a substantially impermeable polymer layer and the liquid core comprises carbonatogenic bacterial spores and bacterial nutrients dispersed in a liquid medium.

In this fourth aspect of the invention, the nutrients are co-encapsulated with the carbonatogenic bacterial spores in the microcapsules, regardless of the concentration or variety of the bacterial spores (other than being carbonatogenic), the nature of the polymer layer and the nature of the liquid medium.

As with each of the second and third aspects of the invention, such microcapsules have the ability, once included in a concrete or like material composition, to reduce the area of a defect, such as a crack or an indentation therein, once a quantity of said microcapsules has ruptured, with all the attendant benefits described earlier. Again, such microcapsules may be made by any suitable microencapsulation process, such as those described earlier.

In a preferred embodiment according to the fourth aspect of the invention, when a quantity of such microcapsules is present in the concrete or like material, the area of the defect therein may preferably be reducible by at least 45% as compared to an initial area of the defect once at least some of said quantity of microcapsules have been ruptured. To achieve the percentage reduction in defect area discussed, in each microcapsule, the concentration of the bacterial spores may preferably be at least $10^9$ spores per gram (dry weight) of microcapsule.

Fifth Aspect

In a fifth aspect, the invention provides microcapsules, for inclusion in concrete, concrete-based material and concrete-like material, adapted to reduce the area of a defect in said material once a quantity of said microcapsules has ruptured or is exposed at an interface of the defect, said microcapsules each comprising:
  a porous solid core, comprising a silica-based material, having bacterial nutrients dispersed therein.

Surrounding said porous solid core, there may be provided a surrounding shell, which may also comprise a silica-based material, which may the same as or different to the silica-based material of the core.

As with the previous aspects of the invention, such microcapsules have the ability, once included in a concrete or like material composition, to reduce the area of a defect, such as a crack or an indentation therein, once a quantity of said microcapsules has at least partially released its encapsulated nutrients, with all the attendant benefits described earlier. Again, such microcapsules may be made by any suitable microencapsulation process, such as those described earlier.

In a preferred embodiment according to the fifth aspect of the invention, when a quantity of such microcapsules is present in the concrete or like material, the area of the defect therein may preferably be reducible by at least 45% as compared to an initial area of the defect once at least some of said quantity of microcapsules have been ruptured or exposed at the crack surface. To achieve the percentage reduction in defect area discussed, the microcapsules may have come into contact with humidity and/or water; the bacterial spores may be provided in accordance with any of the previous aspects if the invention and/or by a natural occurrence of such spores in the area surrounding the concrete defect.

Sixth Aspect

In a sixth aspect, the invention provides microcapsules, for inclusion in concrete, concrete-based material and concrete-like material, adapted to reduce the area of a defect in said material once a quantity of said microcapsules has ruptured or is exposed at the interface of the defect, said microcapsules each comprising:
  a porous solid core, comprising a carbohydrate-based material, having carbonatogenic bacterial spores and/or bacterial nutrients dissolved and/or dispersed therein.

Surrounding said porous solid core, there may be provided a surrounding shell, which may also comprise a carbohydrate-based material, which may the same as or different to the carbohydrate-based material of the core.

As with the previous aspects of the invention, such microcapsules have the ability, once included in a concrete or like material composition, to reduce the area of a defect, such as a crack or an indentation therein, once a quantity of said microcapsules has at least partially released its encapsulated nutrients and/or bacterial spores, with all the attendant benefits described earlier. Again, such microcapsules may be made by any suitable microencapsulation process, such as those described earlier.

In a preferred embodiment according to the sixth aspect of the invention, when a quantity of such microcapsules is present in the concrete or like material, the area of the defect therein may preferably be reducible by at least 45% as compared to an initial area of the defect once at least some of said quantity of microcapsules have been ruptured or exposed at the crack surface. To achieve the percentage reduction in defect area discussed, the microcapsules may have come into contact with humidity and/or water (and if not provided in the microcapsules, the bacterial spores may be provided in accordance with any of the previous aspects of the invention and/or by a natural occurrence of such spores in the area surrounding the concrete defect).

Reducible Defect Area

With the microparticles/microcapsules according to any of the previous aspects of the invention, the area of the defect in the concrete or like material may be reducible by at least 50%, preferably by at least 60%, further preferably by at least 70% and most preferably by at least 80% as compared to the initial area of said defect once at least some of said quantity of microparticles/microcapsules have been fractured/ruptured.

Advantageously, the reducible area of the defect may be determined after 4 weeks of continuous wet-dry cycling, beginning with a wet phase which comprises immersion of the concrete or like material, or at least the surface in which the defect is located, in water for 12-20 hours, preferably 16 hours, followed by a dry phase in which the concrete or like material, or at least the surface in which the defect is located, in air (at ambient temperature, such as 20° C., at 50-70%, preferably 60%, relative humidity) for 6-10 hours, preferably 8 hours. Such conditions are believed to facilitate the at least 45 reduction in defect area discussed above.

Polymer Layer

The polymer layer of the microparticles/microcapsules according to any of the previous aspects of the invention may comprise a polymer selected from the group consisting of: gelatines, polyurethanes, polyolefins, polyamides, polysaccharides, silicone resins, epoxy resins, chitosan, aminoplast resins and derivatives and mixtures thereof. These are the same polymers as for the first aspect of the invention. Many of these types of polymeric microcapsule shell materials are further described and exemplified in U.S. Pat. No. 3,870,542.

Preferably, the polymer layer of any of the aforementioned aspects of the invention comprises a polymer selected from the group consisting of: vinyl polymers, acrylate polymers, acrylate-acrylamide copolymers, melamine-formaldehyde polymers, urea-formaldehyde polymers and mixtures and derivatives thereof.

Highly preferred materials for the microcapsule shell wall are aminoplast polymers comprising the reactive products of, for instance, urea or melamine and an aldehyde, e.g. formaldehyde. The polymer layer therefore further preferably may be a melamine formaldehyde resin or include a layer of this polymer. Such materials are those which are capable of acid-condition polymerization from a water-soluble prepolymer or precondensate state. Polymers formed from such precondensate materials under acid conditions are water-insoluble and can provide the requisite microcapsule friability characteristics to allow subsequent rupture of the microcapsule. The microcapsule shell wall may further preferably by formed by a cross-linked network of polymers comprising a melamine-formaldehyde:acrylamide-acrylic acid copolymer.

Microcapsules made from aminoplast polymer shell materials can be made by an interfacial polymerization process, such as is described in U.S. Pat. No. 3,516,941: an aqueous solution of a precondensate (methylol urea) is formed containing from about 3% to 30% by weight of the precondensate. A non-aqueous, water-immiscible liquid is dispersed throughout this solution in the form of microscopically-sized discrete droplets. Whilst maintaining a solution temperature of between 20° C. and 90° C., acid is added to catalyze polymerization of the dissolved precondensate. If the solution is rapidly agitated during this polymerization step, shells of water-insoluble aminoplast polymer form around, so as to encapsulate, the dispersed droplets of liquid forming a liquid core. Microcapsules according to the present invention may be produced by a similar method, with the carbonatogenic bacterial spores and/or bacterial nutrients (as appropriate) being dispersed in the liquid core prior to polymerization.

The polymer layer comprised in the microcapsules of any of the aforementioned aspects of the invention may further comprise reactive functional groups, extending outwardly of the microcapsule, whereby the microcapsule is chemically bondable within the concrete or like material. Such a reactive functional group preferably comprises a reactive moiety adapted to provide covalent bonding within the concrete.

Silica-Based Materials

Suitable silica-based materials for use in accordance with any of the previous aspects of the invention include those made from precursors such as sodium silicate and those selected from organically modified alkoxides ("ORMOSIL") such as tetramethyl orthosilicate (TMOS), tetraethyl orthosilicate (TEOS), methyltrimethoxysilane (MTMS) and mixtures thereof. In general, the encapsulation process used may use silicon precursors of Si—O—Si bonds employed in sol-gel processes. To such silica precursors may be added colloidal silica nanoparticles (such as Ludox™ colloidal silica series), from 0 wt % to 10 wt % of the total silica content, to reinforce the shell and core structure of the obtained microparticles and/or microcapsules.

Many of these types of sol-gel microcapsules are further described and exemplified in EP2335818 A1, U.S. Pat. No. 7,255,874 and U.S. Pat. No. 6,303,149.

Highly preferred precursors for microcapsulation are ORMOSIL comprising the reactive product of TMOS, TEOS and MTMS. Such materials are capable of acid-condition condensation in a compatible solvent or water-soluble monomers or precondensates. Silica-based microparticles and/or microcapsules formed from such monomers and/or precondensate materials under acid conditions may be partially to totally insoluble in the solvents used and thus may provide the requisite microcapsule friability and/or porosity characteristics to allow subsequent release of the nutrients from microcapsules.

By way of example, the following describes the preparation of ORMOSIL microparticles and/or microcapsules containing bacterial nutrients using a sol-gel process:

- dissolve from 0.1 g to 1 g of calcium nitrate and/or from 0.1 g to 1 g of urea in 2 to 5 mL of a 2M hydrochloric acid aqueous solution at room temperature;
- dissolve from 0.01 g to 1 g of a polyethylene glycol sorbitan monooleate surfactant (such as, for example TWEEN™ 80) in the above aqueous mixture;
- optionally add a water suspended solution of colloidal silica nanoparticles (such as Ludox™ colloidal silica series), from 0 wt % to 10 wt % of the total silica content, to the above aqueous mixture;
- dropwise, add the above aqueous mixture to 20 mL to 100 mL of a non-miscible organic solvent (such as cyclohexane, petroleum ether) containing from 0.5 g to 4 g of a sorbitan monooleate surfactant (such as Span™ 80);
- emulsify the resultant biphasic mixture with vigorous agitation until the desired emulsion is reached;
- dropwise, add from 1 to 4 mL of a commercial TEOS solution to the above emulsion whilst mixing;
- continue to stir at room temperature for the desired period of condensation (from 1 to 24 h);
- filter and wash (with previous organic solvents) the resultant silica-based microparticles and/or microcapsules to remove the remaining surfactants, then dry.

Carbohydrate-Based Materials

Suitable carbohydrate-based materials for use in accordance with any of the previous aspects of the invention include those made from precursors such as sodium alginate and those selected from natural source carbohydrate polymers (such as xanthan gums, arabic gums, agar, chitosan, pectin, pullulan, carrageenan, cellulosic materials), oligomers and mixtures thereof. In general, the encapsulation processes used may employ ionic exchange (exchange of sodium ions to calcium or barium ions). To such carbohydrate-based precursors may be added colloidal silica particles (such as Ludox™ colloidal silica series), from 0 wt % to 10 wt % of the total silica content, to reinforce the shell and core structure of the obtained microparticles and/or microcapsules.

Many of these types of alginate microspheres are further described and exemplified in U.S. Pat. No. 5,766,907 A, U.S. Pat. No. 5,508,041A and WO1991/009119 A1.

The most highly preferred precursor for microcapsulation is sodium alginate. Such a material may be capable of gelation and coacervation in compatible solvents. Gelatine-based microcapsules and/or microspheres formed from carbohydrate materials are partially to totally insoluble in the used solvents and can provide the requisite microcapsule friability and/or porosity characteristics to allow subsequent release of the nutrients and/or bacterial spores from microcapsules.

By way of example, the following describes the preparation of sodium alginate microparticles and/or microcapsules containing bacterial nutrients by a sol-gel or coacervation process:

dissolve from 0.1 g to 5 g of urea in 4 mL of water;
added from 1 to 5 wt % of sodium alginate powder to the above and stir the mixture until a homogeneous viscous liquid is obtained;
dropwise, add the above mixture to a calcium-containing solution (preferably of calcium nitrate (for example 25 g/L) and dissolved urea (to avoid a gradient of concentration that will reduce the urea content of the microcapsules and/or microspheres during the shell formation) and stir gently;
filter and dry the resultant alginate-based microparticles and/or microcapsules.

The microparticles and/or microcapsules obtained of any of the aforementioned aspects of the invention may further comprise reactive functional groups on its surface, extending outwardly thereof, whereby the microparticle/microcapsule is chemically bondable within the concrete or like material. Such a reactive functional group preferably comprises a reactive moiety adapted to provide covalent bonding within the concrete.

Bacterial Spores

The bacterial spores according to the any of the previous aspects of the invention may be in the form of a microorganism that is capable of reducing the area of the defect by means of mineral or EPS production, and may be preferably selected from the group of bacteria consisting of: *Bacillus cereus, Bacillus subtilis, Bacillus sphaericus, Bacillus lentus, Bacillus pasteurii, Bacillus megaterium, Bacillus cohnii, Bacillus halodurans, Bacillus pseudofirmas, Myxococcus Xanthus* and mixtures thereof. Such carbonatogenic bacteria, i.e. carbonate- ($CO_3^{2-}$) and bicarbonate- ($HCO_3^-$) producing bacteria, may be used to generate calcium carbonate to achieve the desired concrete (or like material) defect reparation, as will be discussed in more detail below.

Preferably, the bacterial spores of any of the aforementioned aspects of the invention may be selected from the group of bacteria consisting of: *Bacillus sphaericus, Bacillus pasteurii* and *Bacillus cohnii* as being the best performing for present purposes in terms of carbonatogenesis. Further preferably, the bacterial spores may be selected from the group of bacteria consisting of: *Bacillus sphaericus* and *Bacillus pasteurii*.

Liquid

The liquid, preferably a non-aqueous, water-immiscible, of the microcapsules according to the second of third aspects of the invention may be selected from the group consisting of: organic oils, mineral oils, silicone oils, fluorocarbons, fatty acids, plasticizers, esters and mixtures thereof. By "non-aqueous" it is meant that the liquid contains less than 0.1% by weight of water. By "water-immiscible" it is meant that the liquid has less than 1% solubility in water (and vice versa), as this assists in the formation of the microcapsules by an emulsion polymerization route.

It is preferred that the liquid is a silicone oil, preferably having a kinematic viscosity of 500 centistokes ($mm^2$/sec) or less, preferably 350 centistokes ($mm^2$/sec) or less at 25° C.

Size & Content

As noted earlier, microparticles according to the invention may each have average dimensions in the range of from $1 \times 10^{-7}$ m to less than $1 \times 10^{-3}$ m, i.e. from 0.1 to less than 1000 µm, which may be spherical or non-spherical. Microparticles/microcapsules according to any of the aforementioned aspects of the invention may each have an average diameter greater than 0.5 µm, preferably greater than 1 µm. The average diameters of the microparticles/microcapsules may, for example, fall in the range of from 0.5 to 900 µm, of from 0.5 to 500 µm, or of from 1 to 100 µm.

Preferably, the bacterial spores dispersed in the liquid in each microcapsule according to any of the aforementioned aspects of the invention together may amount to 40-70% by volume of the volume within the polymeric shell of each microcapsule.

Further preferably, the bacterial spores may amount to at least 1%, preferably at least 2%, by volume of the volume of the liquid within each microcapsule.

Bacterial Nutrients

By the term "bacterial nutrients" used throughout this specification, it is meant not only nutrients that may be required for germination and/or growth of bacteria, but also the calcium source used by the bacteria to provoke formation of calcium-containing minerals, i.e. the "healing" ingredients. Bacterial nutrients described with respect to the microcapsules of any of the aforementioned aspects of the invention may comprise (but are not limited to): urea ($CO(NH_2)_2$), a suitable carbon and nitrogen source, such as nutrient broth, yeast, yeast extract, organic oil and a suitable source of calcium, such as hydrated calcium nitrate ($Ca(NO_3)_2.4H_2O$), calcium chloride, calcium acetate, calcium lactate and the like.

In addition to provision of novel and inventive microcapsules per se, the present invention also provides novel and inventive concrete compositions, which are "self-healing", containing such microcapsules.

Seventh Aspect

Accordingly, a seventh aspect of the present invention provides a concrete, concrete-based material and concrete-like material composition comprising:

a cementitious material, one or more aggregate materials, a liquid binder and a quantity of microparticles/microcapsules according to any of the previous aspects of the invention, whereby, once set into concrete, the area of a defect therein is reducible by at least 45% as compared to an initial area of the defect once at least some of said quantity of microcapsules have been ruptured.

Eighth Aspect

An eighth aspect of the present invention provides a concrete, concrete-based material and concrete-like material composition comprising:

a cementitious material, one or more aggregate materials, a liquid binder and a quantity of microparticles/microcapsules according to any of the previous aspects of the invention.

Ninth Aspect

A ninth aspect of the present invention provides a method of reducing the area of a defect (as compared to an initial area of the defect) in concrete, concrete-based material and/or concrete-like material comprising the steps of:
(i) providing a concrete, concrete-based material and/or concrete-like material composition according to the seventh and/or eighth aspects of the invention incorporating a quantity of microparticles/microcapsules;
(ii) setting the composition; and
(iii) causing at least some of said quantity of microparticles/microcapsules to fracture/rupture in response to the creation and/or worsening of a defect in said set composition, thereby releasing their contents to effect defect reduction.

Once set into concrete, the area of a defect therein may be reducible by at least 45 as compared to an initial area of the defect once at least some of said quantity of microparticles/microcapsules has been fractured/ruptured.

The presence of microparticles/microcapsules according to any of the aforementioned aspects of the invention into such concrete or like material compositions mean the area of a defect, such as a crack or an indentation therein, is reducible by at least 45 once a quantity of said microparticles/microcapsules has fractured/ruptured, i.e. a degree of self-repair is achievable. Fracture/rupture of the microparticles/microcapsules is achieved by locally induced internal stress in the concrete around the area of the defect, however, an external influence such as force or increased/decreased temperature, may be applied in addition to the internal stress to act on the inherent friability of the microparticles/microcapsules to achieve fracture/rupture. Once fractured/ruptured, the relevant microparticles/microcapsules will release their (encapsulated) contents, thus facilitating repair of the defect in as timely a manner as possible to provide a compatible and durable solution.

For the avoidance of doubt, the fracture/rupture of as few as a single microparticle/microcapsule would facilitate some degree of defect area reduction, however for the results to be non-negligible and for a discernible reparation to be observed, a quantity of microparticles/microcapsules (being greater in number than a single microparticle/microcapsule, preferably at least $10^4$ microparticles/microcapsules per cm$^2$ of defect area, and generally of the order of $10^6$ microparticles/microcapsules per cm$^2$ of defect area) are required to fracture/rupture.

Surprisingly, the inventors found that the bacterial spores were able to withstand the manufacturing (e.g. microencapsulation) process, such that they were still able to germinate, and for ureolytic activity to decompose urea (present in bacterial nutrients) to begin. The bacterial spores thus remain dormant inside the microparticles/microcapsules.

Without wishing to be bound by any theory, the repair mechanism is thought to follow the following pathway:
(1) Fracture/rupture of microparticle/microcapsule→release of bacterial spores, for exposure to germination activators: oxygen, water and bacterial nutrients
(2) Germination of bacterial spores→production of vegetative bacterial cells for use in hydrolysis
(3) Precipitation of calcium carbonate for defect repair via:

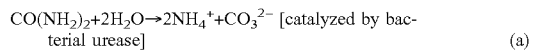

(a)

(b)

Defect formation, for example formation of a crack, triggers breakage of the microparticles/microcapsules in the vicinity of the crack, which enables exposure of the liquid core. In the presence of oxygen, water and bacterial nutrients, the bacterial spores in the liquid core begin to germinate so that ureolytic activity may begin. Urea is decomposed into $CO_3^{2-}$ and $NH_3/NH_4^+$ by the germinated bacteria (catalyzed by bacterial urease) under alkaline pH. When $CO_3^{2-}$ ions meet with $Ca^{2+}$ ions (e.g. from calcium nitrate), $CaCO_3$ is formed.

A concrete composition according to either the seventh or eighth aspects of the invention, which may include carbonatogenic bacterial spore-containing microparticles/microcapsules according to any of the previous aspects of the invention, is thus advantageous over prior art concrete compositions in that it possesses the desired interface compatibility between the walls of a defect in the concrete and the in-situ generated calcium carbonate used for repair. Furthermore, there is no limit to the extent to which the in-situ generated calcium carbonate is generated to enable repair of the defect provided microparticles/microcapsules are evenly distributed throughout the concrete composition. Moreover, because of the compatibility of the repair material with the concrete, the repair possesses the desired longevity and durability. Also, any consequential effects (such as localized weakening) on the concrete immediately surrounding the repaired crack are minimized, again because of the compatibility of the repair material with the concrete.

The area of the defect in the concrete formable from the composition of either the seventh or eighth aspect of the invention may be reducible by at least 50%, preferably by at least 60%, further preferably by at least 70% and most preferably by at least 80 as compared to the initial area of said defect once at least some of said quantity of microparticles/microcapsules have been fractured/ruptured.

Advantageously, the reducible area of the defect may be determined after 4 weeks of continuous wet-dry cycling, beginning with a wet phase which comprises immersion of the concrete or like material, or at least the surface in which the defect is located, in water for 12-20 hours, preferably 16 hours, followed by a dry phase in which the concrete or like material, or at least the surface in which the defect is located, in air (at ambient temperature, such as 20° C., at 50-70%, preferably 60%, relative humidity) for 6-10 hours, preferably 8 hours. Such conditions are believed to facilitate the at least 45 reduction in defect area discussed above.

Microparticles/Microcapsule Dosage

Advantageously, the quantity of microparticles/microcapsules comprised in the composition according to either the seventh or eighth aspects of the invention, based on their dry weight, is in the range of 1% to 10%, preferably 2% to 8%, by weight of the cementitious material.

In one embodiment, the microparticles/microcapsules may be added to the composition in the form of an emulsion having the microparticles/microcapsules dispersed therein, particular when the microparticles/microcapsules have been formed by an emulsion polymerization method. Further preferably, the emulsion may be a water-based emulsion.

Bacterial Nutrients

A concrete composition according to the seventh or eighth aspects of the invention may comprise or further comprise bacterial nutrients, which are preferably added to the concrete composition per se alongside the cementitious material, aggregate material, liquid binder and microparticles/microcapsules, which may or may not themselves also contain bacterial nutrients.

The bacterial nutrients may be thus incorporated into the composition by any one or more of the following means:
by direct admixture into the composition;
by admixture of a quantity of different microcapsules containing the nutrients;

by admixture of a hydrogel or other such suitable carrier, e.g. porous aggregate, clays or diatomaceous earth, containing the nutrients.

The quantity of bacterial nutrients comprised in the composition may beneficially be in the range of 10% to 20%, preferably 12% to 18%, by weight of the cementitious material.

Concrete Ingredients

In a concrete composition according to the seventh and eighth aspects of the invention, the cementitious material is preferably cement. A typically suitable cement is Portland cement, however any other suitable cementitious material may be used.

In a concrete composition according to the seventh and eighth aspects of the invention, the aggregate material is preferably a mixture of fine and coarse aggregates, of differing particles sizes, including materials such as sand, natural gravel, crushed stone and/or recycled materials obtained from construction, demolition and/or excavation waste.

In a concrete composition according to the seventh and eighth aspects of the invention, the liquid binder is preferably water.

Advantageously, the ratio of cementitious material to aggregate material to water in a concrete composition according to the seventh and eighth aspects of the invention may be in the ranges of (0.5 to 1.5):(1 to 15):(0.1 to 1), with the ratio 1:5:0.5 being preferred.

For a better understanding, the present invention will now be more particularly described by way of non-limiting examples only, with reference to the accompanying Figures in which.

Figure 8:
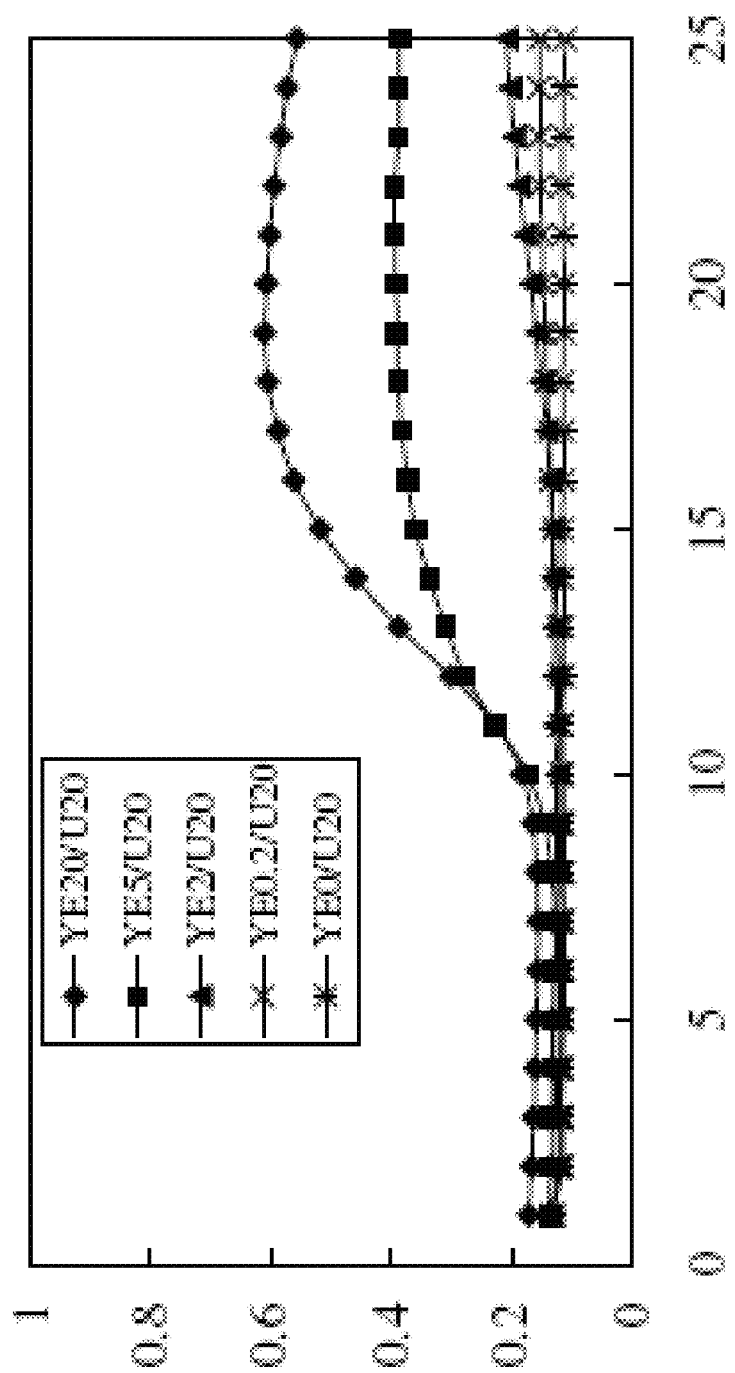

FIG. 8 is a plot of the absolute concentration of bacterial cells against time (hours) for varying concentrations (g/L) of nutrient at a fixed concentration (g/L) of urea; and FIG. 9 is a series of plots (a) to (c) showing the degree of bacterial spore germination under different temperature conditions (28° C., 20° C. and 10° C. respectively) by measuring the concentration (g/L) of urea decomposed over time (days) for varying concentrations (g/L) of nutrient at a fixed initial concentration (g/L) of urea.

Six example cement compositions were prepared, as detailed in Table 1 below. The "Group R" specimens are the control specimens, prepared without any additions to the basic cement, sand and water composition. The "Group N" specimens were prepared with bacterial nutrients of (i) yeast, (ii) urea and (iii) calcium nitrate tetrahydrate in amounts of 0.85%, 4% and 8% by weight of cement as the only additions as compared to the control specimens. The "Group C" specimens were prepared with control microcapsules (containing no bacterial spores) in an amount of 3% by weight of cement. Thus the "Group NC" specimens were prepared as per the "Group N" and "Group C" specimens combined, with both bacterial nutrients and 3% by weight of microcapsules containing no bacterial spores. The "Group NCS3%" and "Group NCS5%" were prepared containing bacterial nutrients (as per the "Group N" specimens) and 3% and 5% (by weight of cement) respectively microcapsules containing encapsulated bacterial spores in a concentration of $10^9$ spores per gram (dry weight) of microcapsule.

TABLE 1

| Group | Cement (g) | Sand (g) | Water (g) | Bacterial Nutrients (g) | Microcapsule Emulsion (g) | Dry Weight of Microcapsules (g) | Bacterial Spores? |
|---|---|---|---|---|---|---|---|
| R | 450 | 1350 | 225 | 0 | 0 | 0 | N |
| N | 450 | 1350 | 214 | 57.84 | 0 | 0 | N |
| C | 450 | 1350 | 212.4 | 0 | 26.1 | 13.5 | N |
| NC | 450 | 1350 | 201.4 | 57.84 | 26.1 | 13.5 | N |
| NCS 3% | 450 | 1350 | 192.8 | 57.84 | 34.7 | 13.5 | Y |
| NCS 5% | 450 | 1350 | 178.7 | 57.84 | 57.84 | 22.5 | Y |

In the specimens having bacterial nutrients added (Groups N, NC, NCS3% and NCS5%), to offset the 30.5 wt % provided by the water of hydration in the calcium nitrate tetrahydrate, the amount of water added to the composition was accordingly reduced from 225 g. Similarly, in the specimens having microcapsules added (Groups C, NC, NCS3% and NCS 5%), to offset the water provided from the emulsion (in which the microcapsules were added to the compositions), the amount of water added to the composition was accordingly reduced, or further reduced, from 225 g.

For each of the six composition groups, five long reinforced prisms (having dimensions of 30×30×360 mm, with the internal rebar having a length of 660 mm and a diameter of 6 mm) were made—thus thirty specimens in total. After casting, the moulds were placed in an air-conditioned room (at 20° C., >90% RH). The specimens in control Group R were de-moulded after 24 hours, while the specimens in other Groups were de-moulded after 48 hours because of their slower hardening in the first 24 hours due to the additives. After de-moulding, all specimens were stored in the same air conditioned room until the time of testing.

28 days after casting, each of the long reinforced prisms were subjected to a tensile test to create multiple cracks. The rebar of the prism was clamped into a test machine (Amsler 100, SZDU 230, Switzerland), with the distance between the clamp and the side surface of the prism being 50 mm. After unloading, the rebar was cut off (leaving around 140 mm protruding from each end of the prisms) and the remaining rebar was wrapped with aluminium tape to prevent iron corrosion during subsequent immersion.

After crack creation, the long reinforced prisms were subjected to five incubation conditions:

(1) 20° C., >90% RH (2) full and continuous immersion in water (3) full and continuous immersion in a deposition medium (4) continuous wet-dry cycling with water (5) continuous wet-dry cycling with the deposition medium.

The deposition medium was composed of 0.2 M urea and 0.2 M $Ca(NO_3)_2$.

During the wet-dry cycles, the specimens were immersed in water/deposition medium for 16 hours and then exposed to air for 8 hours. The incubation conditions of (2), (3), (4) and (5) were performed in an air-conditioned room (20° C., 60% RH). When the specimens were subjected to immersion, they were not in contact with the bottom of the immersion container but some distance (about 5 mm) was maintained in between. Four 360 mm×30 mm surfaces were named A, B, C and D to represent different contact conditions with water: surfaces B and C were the upper and lower surfaces, while surfaces A and D were the two side surfaces, respectively.

The cracks formed in each specimen, per incubation condition, were identified and counted; the results are shown in Table 2 below.

TABLE 2

| Group | Incubation Condition | No. of Cracks per Surface | | | | Total No. of Cracks per Specimen |
|---|---|---|---|---|---|---|
| | | Surface A | Surface B | Surface C | Surface D | |
| R | (1) | 8 | 8 | 8 | 7 | 31 |
| | (2) | 5 | 6 | 5 | 6 | 22 |
| | (3) | 6 | 6 | 5 | 6 | 23 |
| | (4) | 7 | 6 | 6 | 5 | 24 |
| | (5) | 6 | 6 | 6 | 5 | 23 |
| N | (1) | 6 | 6 | 5 | 6 | 23 |
| | (2) | 6 | 7 | 6 | 7 | 26 |
| | (3) | 7 | 5 | 5 | 6 | 23 |
| | (4) | 8 | 7 | 8 | 8 | 31 |
| | (5) | 6 | 6 | 6 | 6 | 24 |
| C | (1) | 4 | 3 | 3 | 3 | 13 |
| | (2) | 3 | 4 | 4 | 4 | 15 |
| | (3) | 4 | 4 | 4 | 5 | 17 |
| | (4) | 4 | 4 | 4 | 4 | 16 |
| | (5) | 5 | 5 | 5 | 5 | 20 |
| NC | (1) | 7 | 6 | 5 | 6 | 24 |
| | (2) | 5 | 6 | 6 | 6 | 23 |
| | (3) | 5 | 5 | 6 | 6 | 22 |
| | (4) | 7 | 6 | 8 | 7 | 28 |
| | (5) | 5 | 7 | 7 | 6 | 25 |
| NCS3% | (1) | 10 | 7 | 9 | 9 | 35 |
| | (2) | 4 | 6 | 6 | 4 | 20 |
| | (3) | 10 | 9 | 7 | 6 | 32 |
| | (4) | 7 | 4 | 6 | 7 | 24 |
| | (5) | 5 | 5 | 5 | 5 | 20 |
| NCS5% | (1) | 4 | 3 | 2 | 5 | 14 |
| | (2) | 4 | 5 | 4 | 5 | 18 |
| | (3) | 9 | 5 | 5 | 5 | 24 |
| | (4) | 4 | 9 | 7 | 7 | 27 |
| | (5) | 9 | 7 | 5 | 5 | 26 |

Initial optical microscope images of the cracks in the specimens were taken immediately after multiple cracking. Each crack was divided into 10-11 portions by pencil markers to make sure the whole crack would be photomicrographed with minimal overlap of the area among the images.

During the incubation period under different conditions, the specimens were subjected to light microscopy every week in the first month and at the end of the second month. The values of the initial and final cracking area in the images were determined by a Leica™ image analysis program.

Although the same methodology was applied to create cracks in each of the specimens, the cracking behaviour was clearly different due to different mechanical properties of the specimens, on account of their different compositions. As shown in Table 2, the number of cracks per specimen varied from 13 to 35 and the crack widths varied from 50 μm to 900 μm.

The self-healing efficiency, or extent of defect (crack) repair, of each of the samples was evaluated by determination of the absolute healed cracking area ($A_h$).

Crack healing efficiency was also evaluated by the healing ratio (the amount of crack area filled by the precipitation), which was calculated based on the equation shown below. The healing ratio can indicate the potential healing effect in the absence of specific information about the cracks (widths, area, etc.) in practice.

$$r = \frac{A_i - A_f}{A_i} \times 100\%$$

where:

"r" is the crack healing ratio

"$A_i$" is the initial crack area ($mm^2$)

"$A_f$" is the final crack area ($mm^2$)

It was clearly observed that the crack area gradually decreased over time. Within three weeks, the crack area was almost completely healed. However, in order to quantify the healing efficiency, the cumulative healed crack area in each specimen after eight weeks was calculated based on its total initial ($A_i$) and total final ($A_f$) crack area, which is shown in accompanying FIG. 1.

As shown in FIG. 1, the crack area was decreased after eight weeks in all specimens (shown in plots (a) to (f)) except for those incubated under condition (1) (in an air-conditioned room at 20° C. at 95% RH), in which no obvious healing was visualized under light microscopy. In each plot, a set of "paired" bars is plotted per incubation condition (1) to (5), with the total initial crack area ($A_i$) being represented by the left hand bar in each pair, and the total final crack area ($A_f$) being represented by the right hand bar in each pair.

Figure 1A:
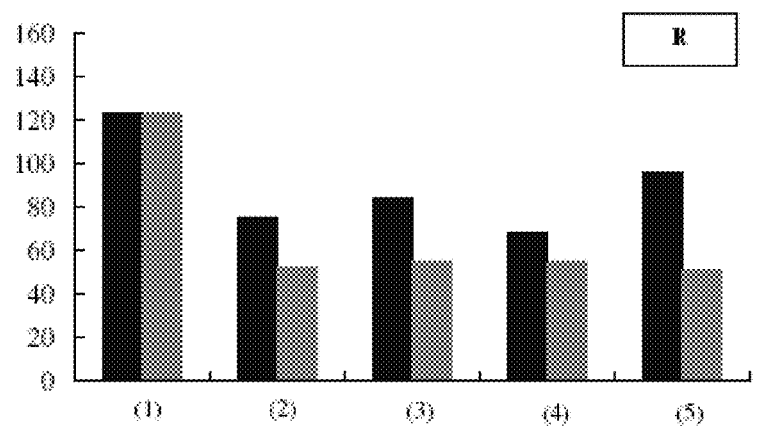
FIG. 1 illustrates a series of plots (a) to (f) for a number of different cement samples (Groups R, N, C, NC, NCS3% and NCS5% respectively) of initial crack area (mm$^2$) compared to final crack area (mm$^2$) after being subjected to different incubation conditions (1) to (5)
Figure 1B:
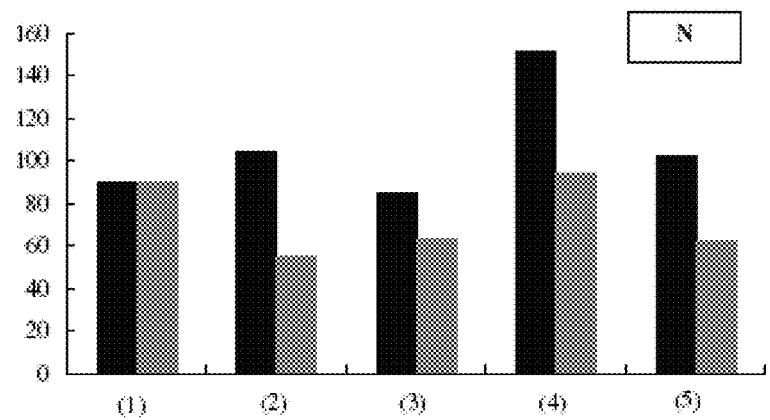
Figure 1C:
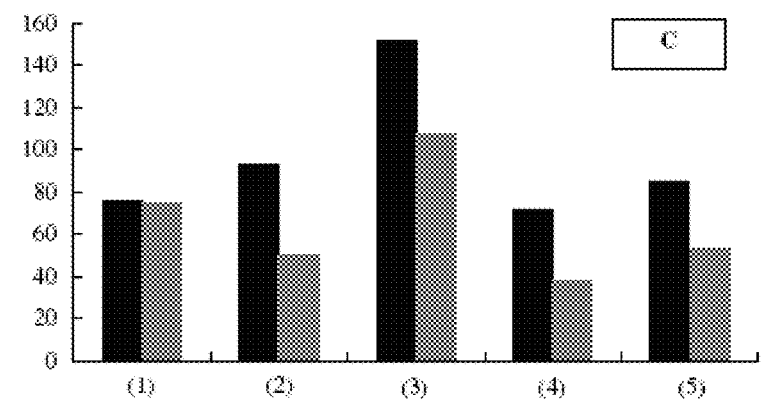
Figure 1D:
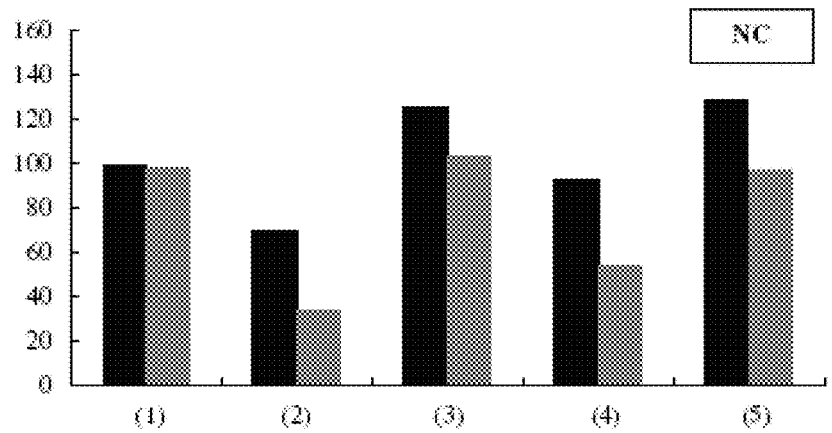
Figure 1E:
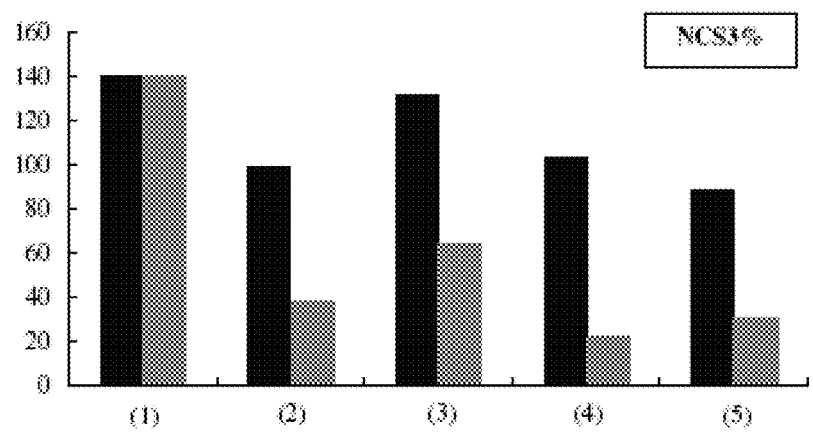
Figure 1F:
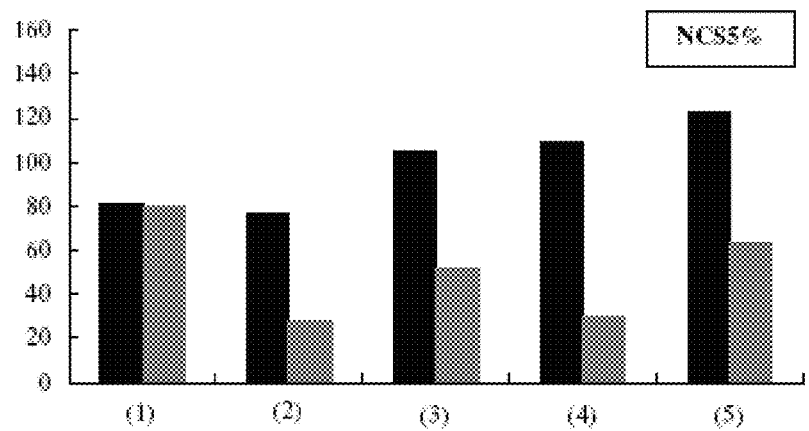
Figure 2:
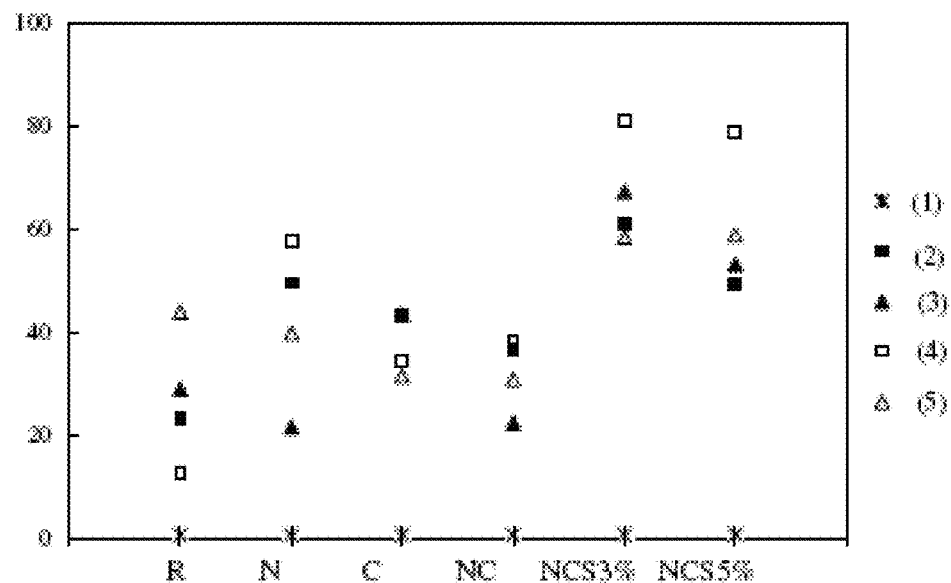
FIG. 2 is a plot of the absolute value of healed crack area (mm$^2$) for the cement samples shown in FIGS. 1(a) to 1(f) for incubation conditions (1) to (5)
Figure 3:
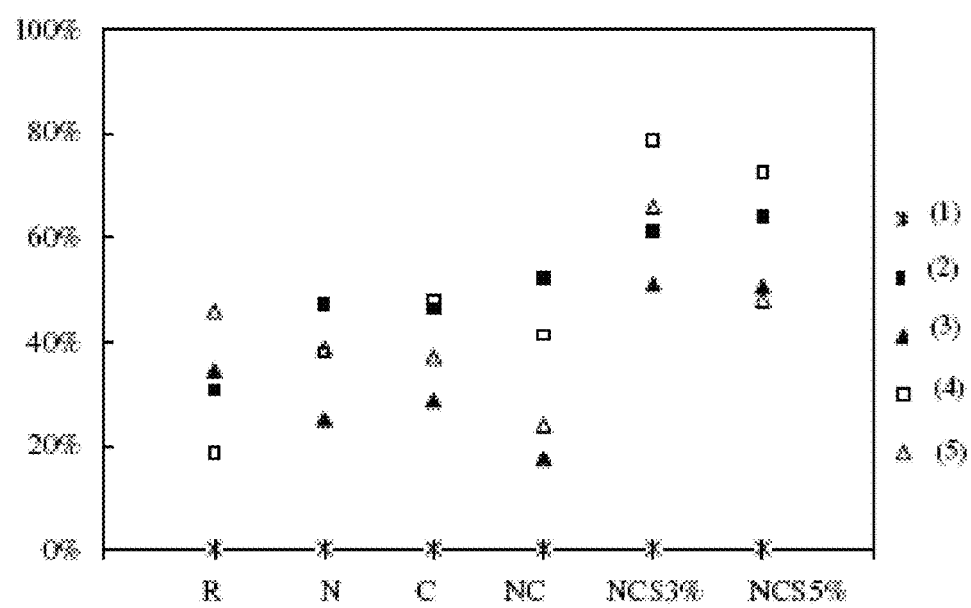
FIG. 3 is a plot of the healing ratio for the cement samples shown in FIGS. 1(a) to 1(f) and FIG. 2 for incubation conditions (1) to (5)

The absolute value of the healed crack area ($A_h$) shown in FIG. 2 provides a straight comparison of healing efficiency, while the healing ratio (r) provides a means to compare healing efficiencies relative to the original crack area per specimen as shown in FIG. 3.

Crack healing was observed in all specimens except for those stored at 95% RH. For the specimens without microencapsulated bacteria, a considerable amount of crack healing (autogenous healing) was observed when they were subjected to submersion or wet-dry cycles. The healed crack area ($A_h$) varied from 12.6 mm$^2$ to 57.8 mm$^2$ depending on the specific specimen and its incubation condition.

Compared with the specimens without encapsulated bacteria, those with microencapsulated bacteria showed much higher healing efficiency (r). The healed crack area ($A_h$) varied from 49.3 mm$^2$ to 80 mm$^2$. In view of the overall healed crack area, no significant difference was observed between the series of NCS3% and NCS5%, however, the specific healing efficiency of each specimen of NCS3% and NCS5% was different depending on the incubation conditions. The maximum healed crack area (around 80 mm$^2$) was observed in the specimens which were subjected to the condition of wet-dry cycles with water, although the specimens under other incubation conditions exhibited similar healing efficiencies.

The crack healing ratio (r) in each specimen of the different series is shown in FIG. 3. The specimens without encapsulated bacteria had a healing ratio (r) in the range of 18% to 50%. No significant difference in the overall healing ratio (r) was observed among different series (R, N, C and NC).

The specimens with microencapsulated bacteria had a much higher healing ratio (r) which ranged from 48% to 80%. The highest value was obtained in the specimen of NCS3%, which was subjected to incubation condition (4).

The specimens with microencapsulated bacteria incorporated showed much higher self-healing efficiency; around six times the crack area was healed compared with the control "Group R" series when the specimens were subjected to incubation condition (4). In view of the healed crack area, the specimens in non-bacterial groups (R, N, C, NC) had a healed area range of 12.6 mm$^2$ to 57.8 mm$^2$ while the bacterial-containing groups (NCS3% and NCS5%) had 49.3 mm$^2$ to 80 mm$^2$ of the crack area healed. The maximum crack width healed in the specimens of the bacterial-containing groups was 970 μm, which was much wider than that in the specimens of non-bacterial groups (maximum 250 μm).

Figure 4:
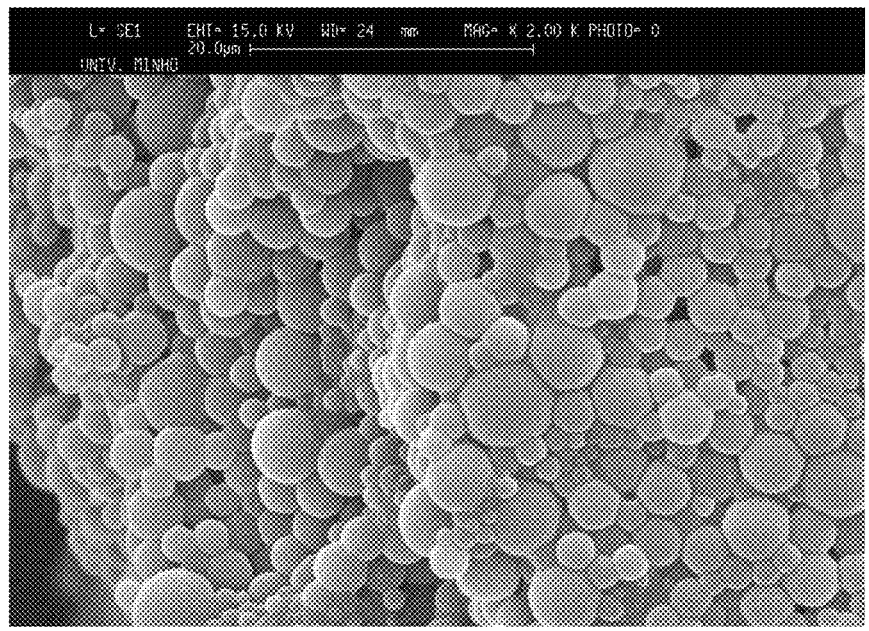
FIG. 4 is a scanning electron microscope (SEM) micrograph of a quantity of aminoplast microcapsules according to one embodiment of the invention.
Figure 5:
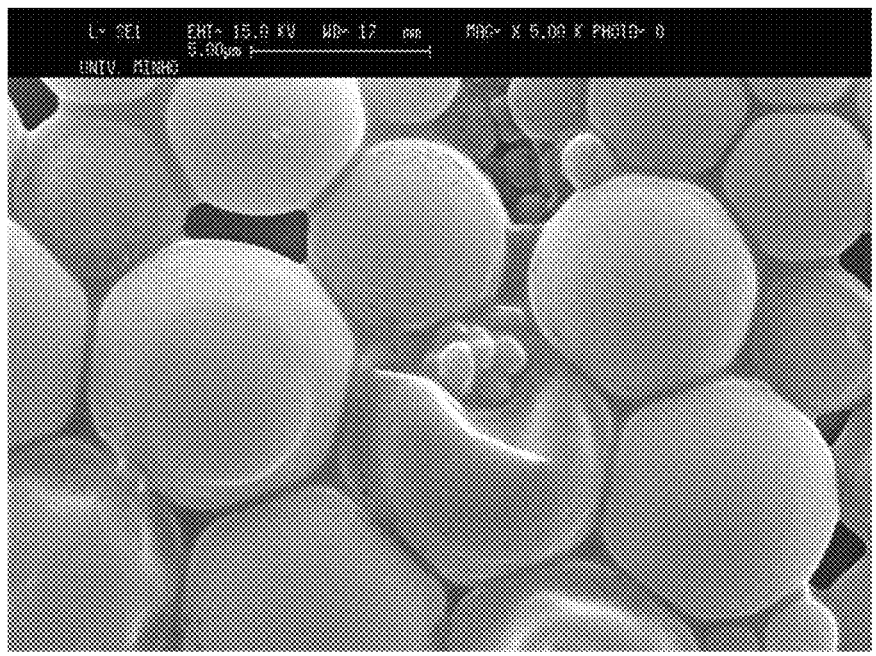
FIG. 5 is an SEM micrograph of the quantity of aminoplast microcapsules shown in FIG. 4 but at greater magnification.

The micrograph of FIG. 4 shows a quantity of microcapsules having an aminoplast shell containing bacterial spores and bacterial nutrients in the form of yeast extract. The magnified micrograph of FIG. 5 shows a number of the quantity of said microcapsules having been ruptured, such that a number of bacterial spores along with its surround yeast extract is released from those number of microcapsules.

Figure 6:
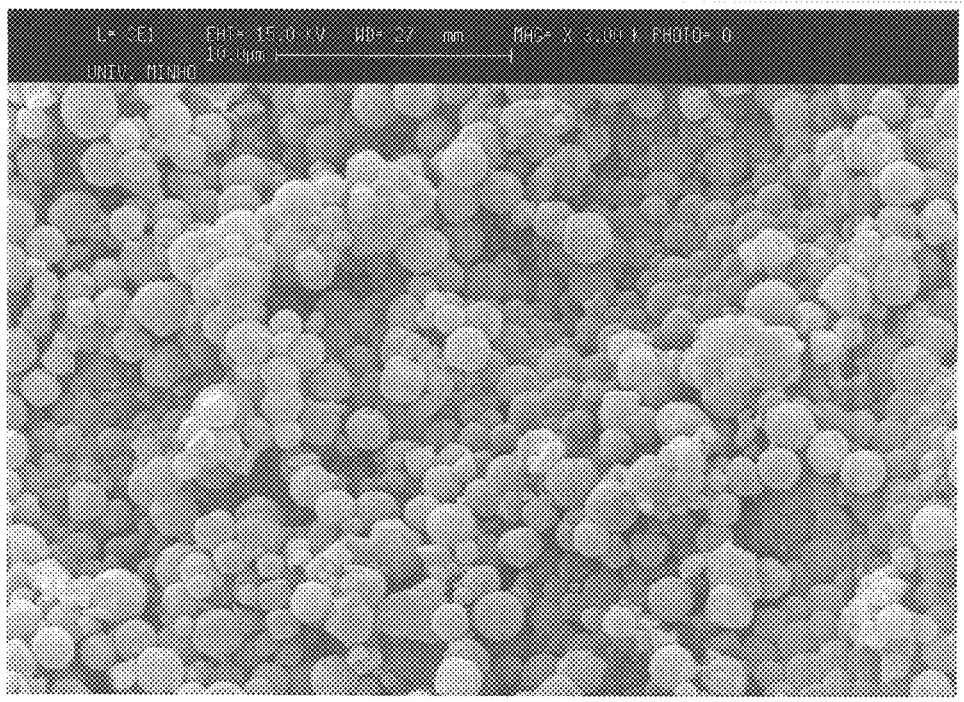
FIG. 6 is an SEM micrograph of a quantity of silica-based material microparticles/microcapsules according to another embodiment of the invention.
Figure 7:
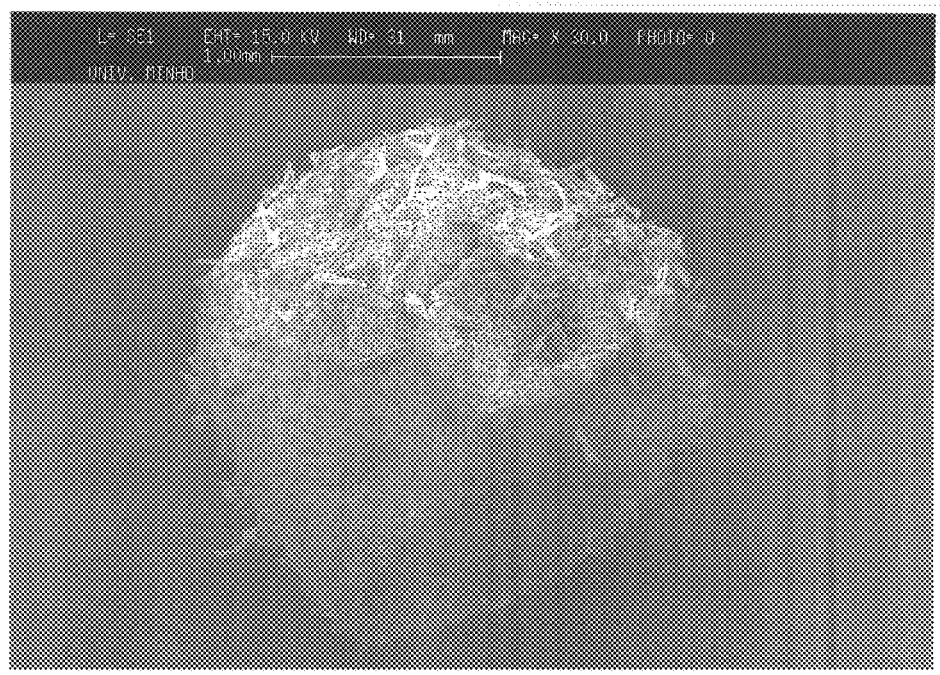
FIG. 7 is an SEM micrograph of an alginate microparticle according to a further embodiment of the invention.

The SEM micrograph images of FIGS. 6 and 7 respectively show a quantity of microparticles/microcapsules having a silica-based material core and/or shell containing only bacterial nutrients and a microparticle of alginate core material containing only bacterial nutrients.

The plots shown in FIGS. 8 and 9 are a result of further investigative work undertaken to determine the effect of a particular bacterial nutrient (yeast extract "YE") on the activity of bacterial spores, in particular the germination and outgrowth of spores, and the subsequent formation of bioprecipitation.

FIG. 8 shows that, in a series of media with different concentrations of yeast extract, the higher the concentration of yeast extract (from 0 g/L to 20 g/L) for a given initial concentration of urea ("U") (20 g/L), the higher absolute concentration of bacterial cells present, particularly after a period of fifteen hours. Clearly, the outgrowth of spores was much more remarkable at YE20/U20 and YE5/U20 than in other series with lower concentrations of yeast extract.

Figure 9A:
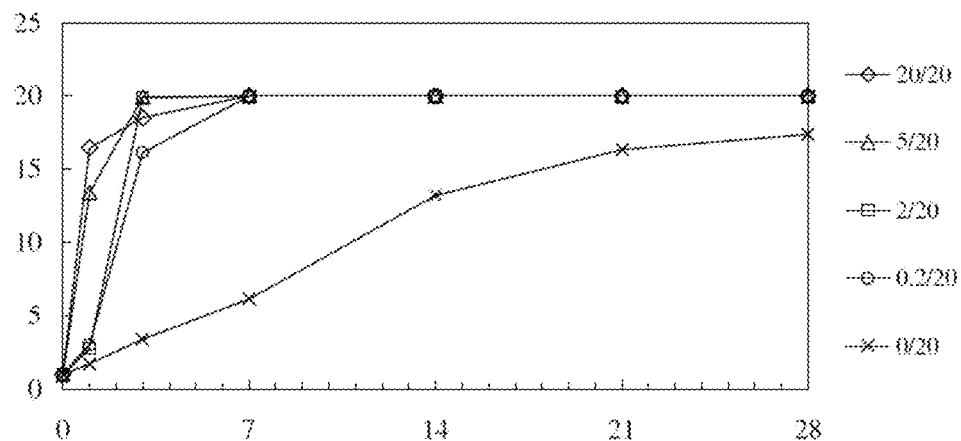
Figure 9B:
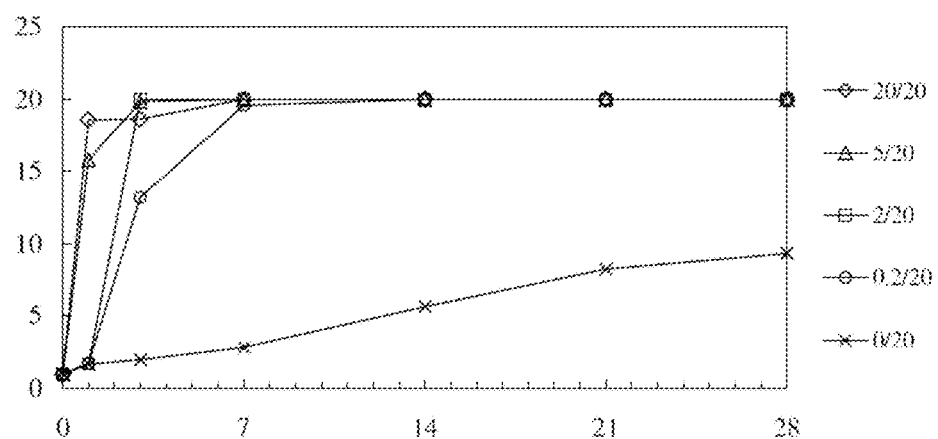
Figure 9C:
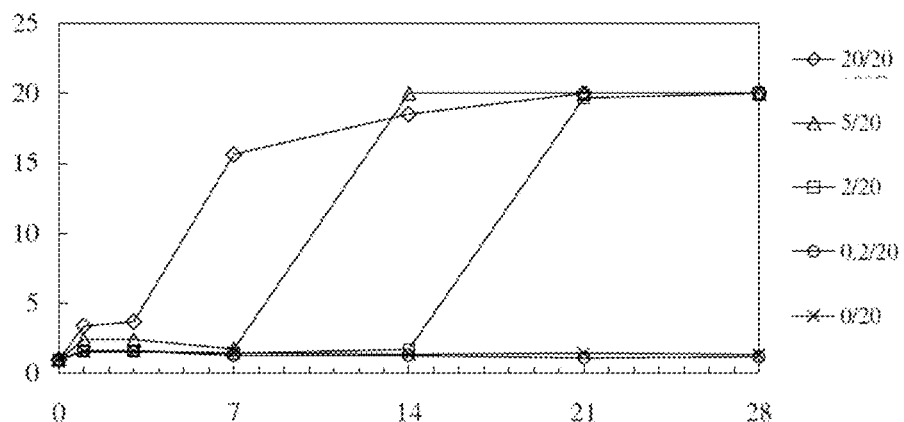

FIGS. 9(a), 9(b) and 9(c) show the variation in germination of B. sphaericus spores at different temperatures (28° C., 20° C. and 10° C. respectively) for different concentrations of yeast extract (m/n in the legend indicates the concentration of yeast extract ("m") and urea ("n") respectively). As shown in FIG. 9(a), at 28° C., spores in the media with yeast extract concentrations of 20 g/L and 5 g/L exhibited a faster revival of ureolytic activity. From around 70% to around 95% of the urea in the media was decomposed in the first day. Spores in the media with 2 g/L and 0.2 g/L yeast extract showed a greatly increased ureolytic activity after 3 days. Within one week, all the urea in the media of yeast extract was completely decomposed. For the spores in the media without yeast extract, the revival of ureolytic activity was much slower but still gradually increased. About 50% (10 g/L) and 85% (17 g/L) of the urea was decomposed after 7 and 28 days respectively. Spores at 20° C. exhibited similar germination behaviour to those at 28° C., as shown in FIG. 9(b).

The revival of spores' ureolytic activity was much slower at 10° C., as shown in FIG. 9(c). In the media with 20 g/L YE, about 3~4 g/L of urea was decomposed in the first 3 days. A significant increase of ureolytic activity occurred between the 3rd and 7th days; 15~17 g/L urea was decomposed by the 7th day. For the media with 5 g/L and 2 g/L YE, the major revival of ureolytic activity occurred between the 7th and 14th days and between the 14th and 21st days respectively. Urea was completely hydrolyzed after 21 days in the media with 20 g/L, 5 g/L and 2 g/L YE. However, the spores in the media with 0.2 g/L and 0 g/L YE showed no noticeable decomposition of urea within 28 days.

It thus appears that, especially when in an unfavourable environment, such as low temperature and in the presence of a high concentration of calcium ions, any negative effect on bacterial ureolytic activity may be counteracted by the presence of yeast extract (YE). Without yeast extract, bacterial spores could still germinate (but without outgrowth) and precipitate $CaCO_3^-$ however precipitation formation was much slower, and that the process only happened at moderate temperatures (20° C.~28° C., not at low temperatures).

Various example embodiments comprise Microparticles, for inclusion in concrete, concrete-based material and concrete-like material, adapted to reduce, or to assist in the reduction of, the area of a defect in said material once a quantity of said microparticles has fractured or is exposed at an interface of the defect, said microparticles may each comprise: a core, in the form of a porous solid and/or a liquid, having carbonatogenic bacterial spores and/or bacterial nutrients dissolved and/or dispersed therein.

In some example embodiments, the core of the microparticles may be provided with a surrounding shell. In some example embodiments, the core has liquid present in substantially all of its pores. In some example embodiments, the core comprises a silica-based material. In some example embodiments, the core comprises a carbohydrate-based material.

Various example embodiments are directed to a concrete composition comprising: a cementitious material, one or more aggregate materials, a liquid binder and a quantity of microparticles, for example, as described herein above.

Various example embodiments are directed to methods of reducing the area of a defect in concrete, concrete-based material and/or concrete-like material. The methods may comprise providing a concrete, concrete-based material and/or concrete-like material composition as described herein above; incorporating a quantity of microparticles; setting the composition; and causing at least some of said quantity of microparticles to fracture in response to the creation and/or worsening of a defect in said set composition, thereby releasing their contents to effect defect reduction.

The invention claimed is:

1. A concrete composition comprising:
a cementitious material;
one or more aggregate materials;
a liquid binder; and
a quantity of microcapsules said microcapsules each further comprising
a polymeric shell encapsulating a liquid core,
wherein the liquid core further comprises carbonatogenic bacterial spores dispersed in a liquid medium and the polymeric shell further comprises a polymer layer substantially impermeable to the liquid core,
such that the quantity of microcapsules is sufficient, so that, once the compositions is set into concrete, the area of a defect therein is reduced by at least 45% by action of the carbonatogenic bacteria as compared to an initial area of the defect after at least some of said quantity of microcapsules have been ruptured.

2. The composition as claimed in claim 1 wherein the liquid core further comprises bacterial nutrients.

3. The composition as claimed in claim 1 wherein the ratio of cementitious material to aggregate material to water is in the ranges of (0.5 to 1.5):(1 to 15):(0.1 to 1).

4. The composition as claimed in claim 1 wherein the quantity of microcapsules comprised in the composition, based on their dry weight, is in the range of 1% to 10%-by weight of the cementitious material.

5. The composition of claim 4, wherein the quantity of microcapsules comprised in the composition, based on their dry weight, is in the range of 2% to 8%, by weight, of the cementitious material.

6. The composition as claimed in claim 1 wherein the microcapsules are added to the composition in the form of an emulsion having the microcapsules dispersed therein.

7. The composition as claimed in claim 6 wherein the emulsion is a water-based emulsion.

8. The composition of claim 1, wherein at least one of the following criteria (i)-(iii) is fulfilled:
(i) said polymer layer comprises a polymer selected from the group consisting of: gelatines, polyurethanes, polyolefins, polyamides, polysaccharides, silicone resins, epoxy resins, chitosan, aminoplast resins, and mixtures thereof, and/or
(ii) said bacterial spores are from a microorganism that is capable of reducing the area of the defect by producing a mineral or extracellular polymeric substance ("EPS") and/or
(iii) said liquid medium is a non-aqueous, water-immiscible liquid selected from the group consisting of: organic oils, mineral oils, silicone oils, fluorocarbons, fatty acids, plasticizers, esters, and mixtures thereof.

9. The composition as claimed in claim 8 wherein any two of the three criteria (i)-(iii) are fulfilled.

10. The composition as claimed in claim 8 wherein all three of criteria (i)-(iii) are fulfilled.

11. The composition claimed in claim 8 wherein, in each microcapsule, the concentration of the bacterial spores is at least $10^9$ spores per gram (dry weight) of microcapsule.

12. A concrete composition comprising:
a cementitious material;
one or more aggregate materials;
a liquid binder; and
a quantity of microcapsules,
the microcapsules further comprising
a polymeric shell encapsulating a liquid core, wherein the liquid core comprises carbonatogenic bacterial spores and bacterial nutrients dispersed in a liquid medium and the polymeric shell comprises a polymer layer substantially impermeable to the liquid core, the quantity of microcapsules being sufficient to reduce the area of a defect in said concrete once said quantity of microcapsules has ruptured or is exposed at an interface of the defect.

13. The composition claimed in claim 1,
wherein, in each microcapsule, the concentration of the bacterial spores is at least $10^9$ spores per gram (dry weight) of microcapsule.

14. The composition as claimed in claim 12 wherein the polymer layer comprises a polymer selected from the group consisting of: gelatines, polyurethanes, polyolefins, polyamides, polysaccharides, silicone resins, epoxy resins, chitosan, aminoplast resins, and mixtures thereof.

15. The composition as claimed in claim 12 wherein the bacterial spores are from a microorganism that is capable of reducing the area of the defect by producing a mineral or extracellular polymeric substance ("EPS").

16. The composition as claimed in claim 12, wherein the liquid medium is selected from the group consisting of: organic oils, mineral oils, silicone oils, fluorocarbons, fatty acids, plasticizers, esters, and mixtures thereof.

17. The composition as claimed in claim 12, wherein the bacterial spores are selected from the group of bacteria consisting of: *Bacillus sphaericus, Bacillus pasteurii* and *Bacillus cohnii*.

18. The composition as claimed in claim 12, wherein the liquid medium is a silicone oil.

19. The composition as claimed in claim 12, wherein the microcapsule each have an average diameter of greater than 0.5 μm.

20. The composition as claimed in claim 12, wherein the bacterial spores dispersed in the liquid medium together amount to 40-70% by volume of the volume within the polymeric shell of each microcapsule.

21. The composition as claimed in claim 12 wherein the bacterial spores amount to at least 1% by volume of the volume of the liquid medium within each microcapsule.

22. The composition as claimed in claim 12, wherein the bacterial nutrients comprise one or more of: urea, a suitable carbon and nitrogen source, such as nutrient broth, yeast, yeast extract, organic oil and a suitable source of calcium, such as hydrated calcium nitrate, calcium chloride, calcium acetate or calcium lactate.

23. The composition as claimed in claim 1, further comprising bacterial nutrients, wherein the bacterial nutrients are incorporated by at least one of direct admixture into the composition, admixture of a quantity of different microcapsules containing the nutrients, admixture of a hydrogel or other such suitable carrier, e.g. porous aggregate, clays or diatomaceous earth, containing the nutrients.

24. The composition as claimed in claim 12, wherein the polymer layer comprises a polymer is selected from the group consisting of: vinyl polymers, acrylate polymers, acrylate-acrylamide copolymers, melamine-formaldehyde polymers, urea-formaldehyde polymers, and mixtures thereof.

25. The composition as claimed in claim 24 wherein the polymer layer comprises melamine formaldehyde resin.

26. The composition as claimed in claim 12, wherein the polymer layer comprises reactive functional groups, extending outwardly of the microcapsule, whereby the microcapsule is chemically bondable within the concrete.

27. The composition as claimed in claim 26, wherein a reactive functional group comprises a reactive moiety adapted to provide covalent bonding within the concrete.

28. The composition as claimed in claim 1, further comprising bacterial nutrients, wherein the quantity of bacterial nutrients comprised in the composition is in the range of 10% to 20%, by weight of the cementitious material.

29. The composition of claim 28, wherein the quantity of bacterial nutrients comprised in the composition is in the range of 12% to 18%, by weight, of the cementitious material.

30. The composition as claimed in claim 12 wherein, the-quantity of said microcapsules present in concrete is sufficient so that the area of the defect therein is reduced by at least 60% by action of the carbonatogenic bacteria as compared to an initial area of the defect after at least some of said quantity of microcapsules have been ruptured.

31. The composition as claimed in claim 30 wherein the quantity of said microcapsules present in concrete is sufficient so that the area of the defect in the concrete is reduced by at least 80% by action of the carbonatogenic bacteria as compared to the initial area of said defect after at least some of said quantity of microcapsules have been ruptured.

32. The composition as claimed in claim 30 wherein the reduced area of the defect is determined after 4 weeks of continuous wet-dry cycling, in which the wet phase comprises immersion of the concrete in water for 16 hours, followed by the dry phase of leaving the concrete in air (at 20° C. at 60% relative humidity) for 8 hours.

33. The composition as claimed in claim 12 wherein, the quantity of microcapsules is sufficient so that once the composition is set into concrete, the area of a defect therein is reduced by at least 70% as compared to an initial area of the defect by action of the carbonatogenic bacteria after at least some of said quantity of microcapsules have been ruptured.

34. The composition as claimed in claim 33 wherein the quantity of microcapsules is sufficient so that the area of the defect in the concrete is reduced by at least 80% by action of the carbonatogenic bacteria as compared to the initial area of said defect after at least some of said quantity of microcapsules have been ruptured.

35. The composition as claimed in claim 33 wherein the reduced area of the defect is determined after 4 weeks of continuous wet-dry cycling, in which the wet phase comprises immersion of the concrete in water for 16 hours, followed by the dry phase of leaving the concrete in air (at 20° C. at 60% relative humidity) for 8 hours.

36. A method of reducing the area of a defect in concrete, concrete-based material and/or concrete-like material comprising the steps of:
(i) providing a concrete, concrete-based material and/or concrete-like material composition as claimed in claim 1 incorporating the quantity of microcapsules;
(ii) setting the composition; and
(iii) causing at least some of said quantity of microcapsules to rupture in response to the creation and/or worsening of a defect in said set composition, thereby releasing their encapsulated contents to effect defect reduction.

\* \* \* \* \*